US012108771B2

United States Patent
Sinskey et al.

(10) Patent No.: US 12,108,771 B2
(45) Date of Patent: Oct. 8, 2024

(54) BEVERAGE COMPOSITIONS COMPRISING WATER-SOLUBLE PALM FRUIT BIOACTIVE COMPLEX/OIL PALM PHENOLICS AND PALM FRUIT JUICE

(71) Applicants: PHENOLAEIS MEXICO SAPI DE CV, Mexico City (MX); Anthony J. Sinskey, Cambridge, MA (US)

(72) Inventors: Anthony J. Sinskey, Cambridge, MA (US); ChoKyun Rha, Cambridge, MA (US); T. G. Sambandan, Cambridge, MA (US); Ravigadevi Sambanthamurthi, Kajang (MY); Anastasia Artamonova, Cambridge, MA (US); Joseph De Angelo, Cambridge, MA (US); Kevin Ohashi, Cambridge, MA (US)

(73) Assignee: PHENOLAEIS MEXICO SAPI DE CV, Mexico City (MX)

( * ) Notice: Subject to any disclaimer, the term of this patent is extended or adjusted under 35 U.S.C. 154(b) by 443 days.

(21) Appl. No.: 17/321,382

(22) Filed: May 14, 2021

(65) Prior Publication Data
US 2022/0039421 A1 Feb. 10, 2022

Related U.S. Application Data

(60) Provisional application No. 63/025,097, filed on May 14, 2020, provisional application No. 63/025,090, filed on May 14, 2020.

(51) Int. Cl.
*A23F 5/46* (2006.01)
*A23L 27/00* (2016.01)
(Continued)

(52) U.S. Cl.
CPC .............. *A23F 5/465* (2013.01); *A23L 27/12* (2016.08); *A23L 27/88* (2016.08); *A23L 33/105* (2016.08);
(Continued)

(58) Field of Classification Search
CPC ............ A23V 2250/21; A23V 2200/15; A23V 2250/2132; A23L 2/52; A23L 33/105;
(Continued)

(56) References Cited

U.S. PATENT DOCUMENTS 6,174,557 B1* 1/2001 Gamez-Rumpf ......... A23F 5/38
426/570
7,387,802 B2* 6/2008 Sambanthamurthi ......................
A61K 36/889
424/727

OTHER PUBLICATIONS

Maifrede P O, BR 102018017157 A2, published Mar. 10, 2020, Machine Translation (Year: 2020).*

* cited by examiner

*Primary Examiner* — Hong T Yoo
(74) *Attorney, Agent, or Firm* — Maschoff Brennan

(57) ABSTRACT

The invention provides a method for enhancing flavour profile of beverages comprising increasing perceptibility of sweetness, increasing acidity, and decreasing astringent taste in beverages, increasing perceptibility of floral and spice notes by adding an effective flavour enhancing amount of water-soluble Palm Fruit Bioactive complex (wsPFBc/OPP) or their extracts into a beverage is disclosed a composition comprising a beverage and oil palm phenolics (OPP) or their extracts such that the OPP or their extracts modify or alter the fragrance and flavour of the beverage.

13 Claims, 8 Drawing Sheets

(51) Int. Cl.
*A23L 27/12* (2016.01)
*A23L 33/105* (2016.01)
*A61K 36/889* (2006.01)

(52) U.S. Cl.
CPC ........ *A61K 36/889* (2013.01); *A23V 2002/00* (2013.01)

(58) Field of Classification Search
CPC ... A23L 2/56; A23L 27/88; A23L 2/04; A23L 27/84; A23L 27/12; A23F 5/465; A62K 36/889
See application file for complete search history.

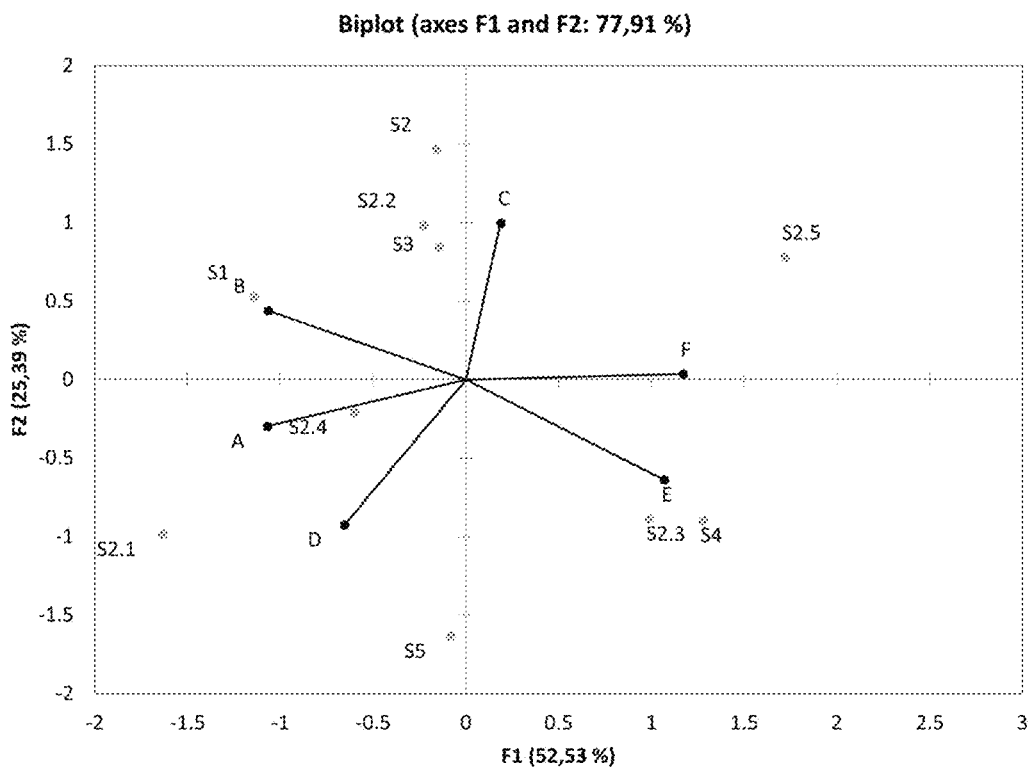
FIG 3.1
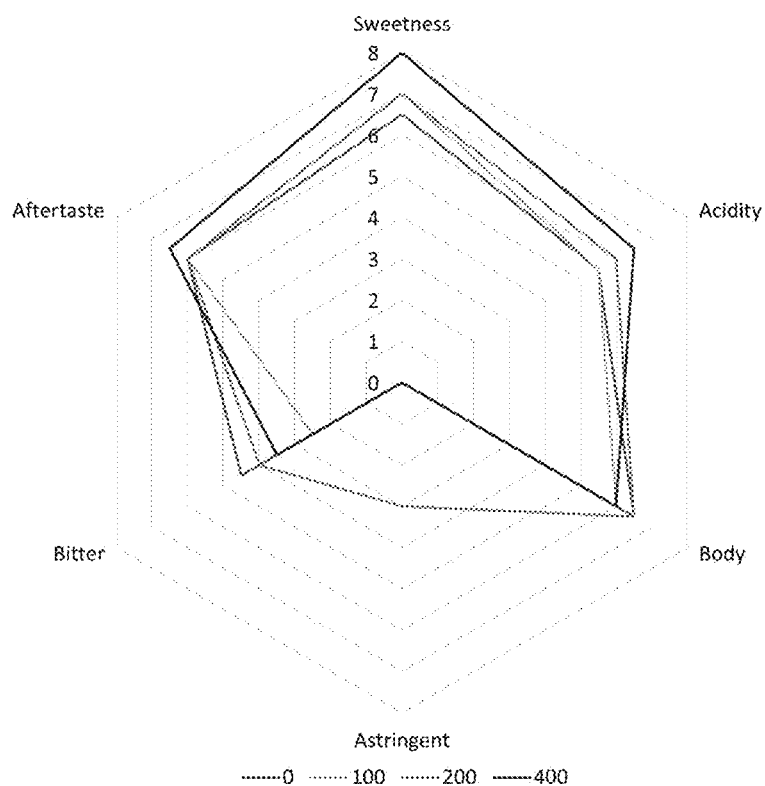
FIG 3.2

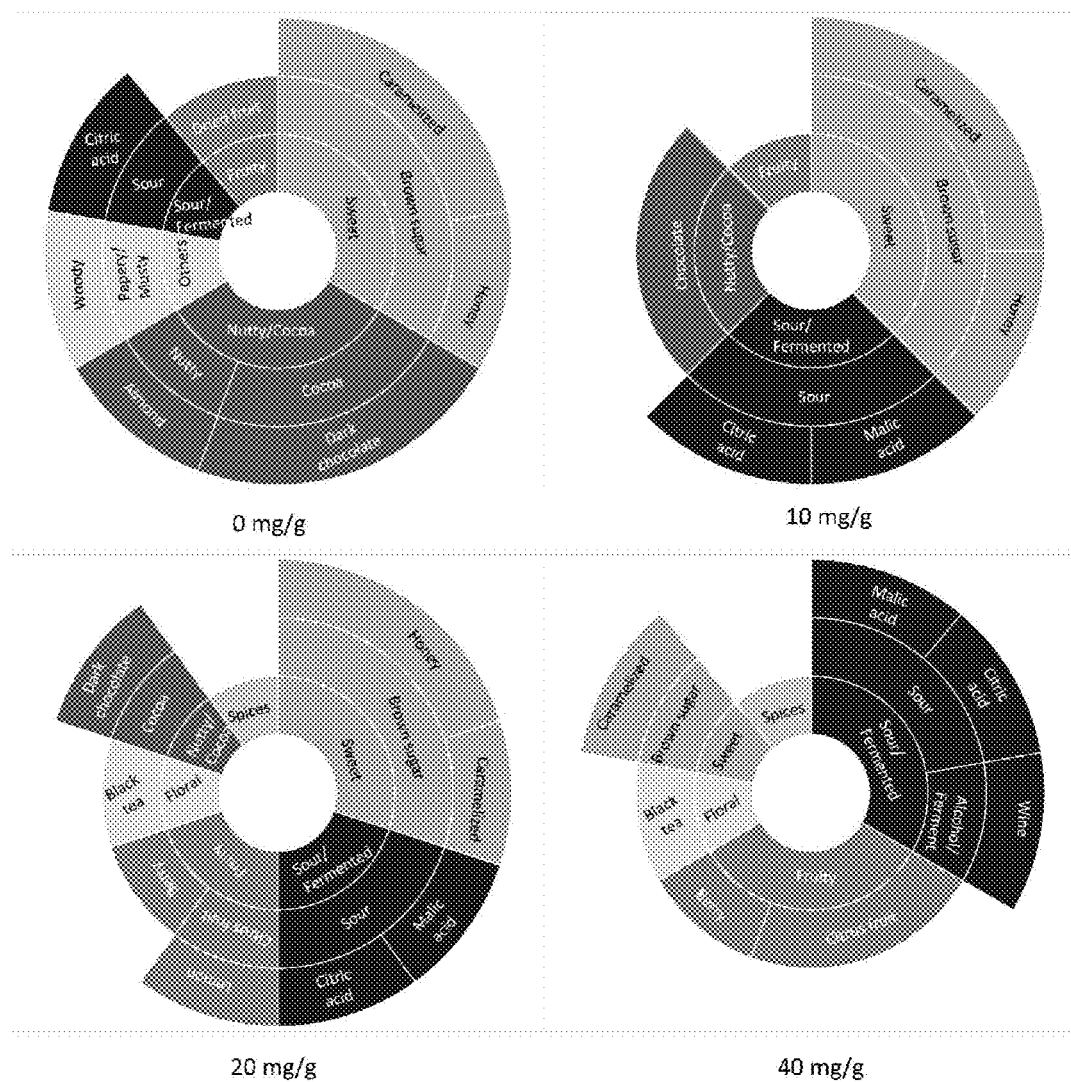
FIG 3.3

BEVERAGE COMPOSITIONS COMPRISING WATER-SOLUBLE PALM FRUIT BIOACTIVE COMPLEX/OIL PALM PHENOLICS AND PALM FRUIT JUICE

FIELD OF INVENTION

The present invention generally relates to coffee, tea, cocoa, and other such beverage compositions such as instant tea/coffee compositions, tea leaves/coffee powder mixes, tea/coffee extracts etc. that include water-soluble palm fruit bioactive complex (wsPFBc), also known as oil palm phenolics (OPP) and palm fruit juice (PFJ), for modifying or altering the characteristics of such beverages. The altered or modified characteristic is flavour and fragrance. The invention also includes the methods of preparation thereof.

BACKGROUND OF THE INVENTION

Phenolic compounds comprise an aromatic ring, bearing one or more hydroxyl substituents, and range from simple phenolic molecules to highly polymerised compounds. Despite this structural diversity, the group of compounds are often referred to as polyphenols. Most naturally occurring phenolic compounds are present as conjugates with mono- and polysaccharides, linked to one or more of the phenolic groups, and may also occur as functional derivatives such as esters and methyl esters.

Phenolic acids consist of two subgroups, i.e., the hydroxybenzoic and hydroxycinnamic acids Hydroxybenzoic acids include gallic, p-hydroxybenzoic, protocatechuic, vanillic and syringic acids, which in common have the $C_6$-$C_1$ structure. Hydroxycinnamic acids, on the other hand, are aromatic compounds with a three-carbon side chain ($C_6$-$C_3$), with caffeic, ferulic, p-coumaric and sinapic acids being the most common.

Phenolic compounds possess different biological activities, but the most important is the antioxidant activity. Their contribution to the antioxidant capacity of the human diet is much larger than that of vitamins. Current evidence strongly supports the contribution of polyphenols to the prevention of cardiovascular diseases, cancers and osteoporosis. They also play a role in the prevention of neurodegenerative diseases and diabetes mellitus.

Phenolic compounds are ubiquitous in plants, and when plant foods are consumed, these phytochemicals contribute to the intake of natural antioxidants in the human diets. Agro-industrial by-products are good sources of phenolic compounds, and have been explored as source of natural antioxidants.

Studies on flavonoids have shown that they are better antioxidants than the nutrients vitamin C, vitamin E and beta-carotene. Therefore, phenolics may be beneficial in preventing UV-induced oxygen free radical generation and lipid peroxidation, i.e. events involved in pathological states such as photoaging and skin cancer. The antioxidant properties of phenolic compounds act as free radical scavengers, hydrogen donators, metal chelators and singlet oxygen quenchers Palm Fruit Bioactive Complex (PFBc)/Oil palm phenolics (OPP) are water-soluble antioxidants derived from the aqueous stream of palm oil milling. They contain flavonoids, polyphenols, phenolic acids, water-soluble vitamins and organic acids.

The major components in PFBc/OPP include p-hydroxybenzoic acid having a general structure as shown, and three isomers of caffeoylshikimic acid. The methyl and propyl esters of p-hydroxybenzoic acid are commonly used in the food industry as anti-microbial agents and in personal care products as preservatives.

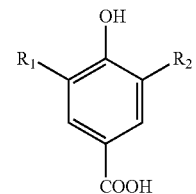

In the existing processes and compositions, there are relatively few existing phenolic type compounds that can the impart fragrance and taste/flavour to beverages. While beverages such as coffee and tea provide numerous health benefits, likewise wsPFBc/OPP and PFJ also provide health benefits such as preventing UV-induced oxygen free radical generation and lipid peroxidation (i.e. events involved in pathological states such as photoaging and skin cancer are absent). Given that tea and coffee being one of the largest consumed beverages, it is therefore desirable to enhance their flavour/fragrance such that they may also impart other health benefits to their existing consumer and a change in flavour/fragrance may induce more people to drink such beverages and thus promoting a healthy lifestyle.

OBJECT OF THE INVENTION

An object of the present invention is to provide edible consumable tea, coffee, cocoa or other such beverage compositions having at least one compound of water-soluble palm fruit bioactive complex (wsPFBc)/oil palm phenolics (OPP) that exhibit highly significant bioactive properties.

Another object of the present invention to provide a composition that includes a combination of phytochemical compounds from varying sources, which if added in food or beverages such as tea/coffee, can modify/improve the characteristics of said food or beverages.

Yet another object of the present invention is to provide a method for modifying or altering the fragrance and/or flavor of beverages such as tea, coffee, cocoa as combined with water-soluble palm fruit bioactive complex (wsPFBc)/oil palm phenolics.

It is further an object of the present invention to provide a composition comprising hydroxybenzoic compound(s) and other related compounds that is useful for enhancing characteristics of edible consumables.

Another object of the present invention to provide a compound, which when added in coffee, improves texture of coffee, and imparts fragrance of vanilla to coffee.

SUMMARY OF THE INVENTION

The present invention relates to a method enhancing flavour profile of beverages comprising the steps of, increasing perceptibility of sweetness, increasing acidity, and decreasing astringent taste in beverages, increasing perceptibility of floral and spice notes by adding an effective flavour enhancing amount of water-soluble Palm Fruit Bioactive complex (wfPFBc/OPP) or their extracts into a beverage.

In one aspect, beverage is coffee, particularly either a commodity coffee or a specialty coffee.

In one aspect the effective flavour enhancing amount of said polyphenols is in a concentration of about 10-80 mg/g, more preferably 20-80 mg/g or 20-40 mg/g, most preferably 30 mg/g wsPFBc in commodity coffees while 40 mg/g in specialty coffees. The flavour enhancing amount is about 3% of the whole wsPFBc and coffee beverage composition composition The present invention further provides a method for enhancing flavour profile of coffee comprising the steps of, roasting coffee beans to produce roasted coffee beans, grinding said roasted coffee beans, preparing a coffee beverage composition, and increasing perceptibility of sweetness, increasing acidity, and decreasing astringent taste in said coffee beverage composition, increasing perceptibility of floral and spice notes by adding an effective flavour enhancing amount of water-soluble Palm Fruit Bioactive complex (wsPFBc/OPP) or their extracts into said coffee beverage composition, ground coffee beans, or roasted coffee beans.

In one aspect, the coffee beverage composition prepared may be provided as instant coffee mix, instant coffee beverage, brewed coffee, espresso, espresso-based coffee beverages, or cold brew.

In another aspect, the coffee beverage composition may be provided as ground coffee, granule mix, powder mix, powder concentrates, liquid mix, liquid concentrates

BRIEF DESCRIPTION OF THE DRAWINGS

FIG. 3.1—Evaluation of the preference of commodity (S1) and specialty (S2) coffees added with wsPFBc. A: most preferred, F: least preferred. 1 (10 mg/g), 2 (20 mg/g), 3 (30 mg/g), 4 (40 mg/g), and 5 (50 mg/g).

FIG. 3.2—Influence of the addition of wsPFBc on the sensory analysis of *Arabica* coffee with concentrations of 0 mg/g, 10 mg/g, 20 mg/g, and 40 mg/g.

FIG. 3.3—Influence of the addition of wsPFBc on the descriptors of *Arabica* coffee.

DETAILED DESCRIPTION OF THE INVENTION

Figure 1:
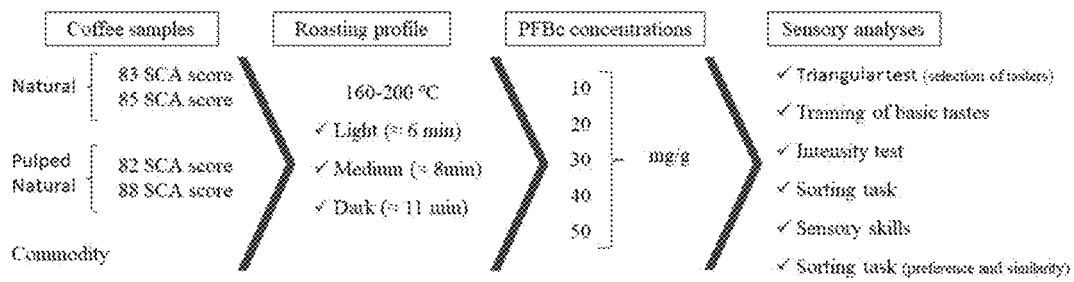
FIG. 1—Block diagram of the raw materials used and sensory analysis steps performed.

The following description includes the preferred best mode of one embodiment of the present invention. It will be clear from this description of the invention that the invention is not limited to these illustrated embodiments but that the invention also includes a variety of modifications, and embodiments thereto. Therefore, the present description should be seen as illustrative and not limiting. While the invention is susceptible to various modifications and alternative constructions, it should be understood, that there is no intention to limit the invention to the specific form disclosed, but, on the contrary, the invention is to cover all modifications, alternative constructions, combinations, and equivalents falling within the spirit and scope of the invention as defined in the claims.

In any embodiment described herein, the open-ended terms "comprising," "comprises," and the like (which are synonymous with "including," "having" and "characterized by") may be replaced by the respective partially closed phrases "consisting essentially of," consists essentially of," and the like or the respective closed phrases "consisting of," "consists of, and the like.

As used herein, the singular forms "a," "an," and "the" designate both the singular and the plural, unless expressly stated to designate the singular only.

In the following description, numerous specific details are set forth in order to provide a thorough understanding of the invention. However, it will be understood by those or ordinary skill in the art that the invention may be practiced without these specific details. In other instances, well known methods, procedures and/or components have not been described in detail so as not to obscure the present embodiment.

The present invention relates to food and beverage compositions for modifying or altering the fragrance, taste and/or flavour of food and/or beverages, comprising water-soluble palm fruit bioactive complex (wsPFBc)/oil palm phenolics (OPP) extracts.

The present invention further relates to methods of improving, modifying or altering the fragrance, taste and/or flavour of food and/or beverages flavour profiles of beverages or beverage compositions comprising water-soluble palm fruit bioactive complex (wsPFBc)/oil palm phenolics (OPP) extracts.

Water-soluble palm fruit bioactive complex (wsPFBc), also called oil palm phenolics (OPP) extracts, is herein referred as to the collective water-soluble phenolic compounds and bioactives of oil palm which is derived from the aqueous waste stream of the palm oil milling process. The wsPFBc/OPP is distinguished from the lipid-soluble bioactives or fat-soluble phytonytrients and/or bioactives of oil palm which is comprised primarily within the main product of the palm oil milling process, the crude palm oil (CPO).

The wsPFBc/OPP is comprised of water-soluble polyphenols such as phenolic acids and other compounds and bioactives of oil palm. Said wsPFBc/OPP may comprise the following major phenolic acids, water-soluble compounds, or water-soluble bioactives found in the aqueous waste stream of the palm oil milling process such as phenolic compounds, and shikimic acid. Phenolic compounds encompassing said wsPFBc/OPP may include, but not limited to caffeoylshikimic acid, caffeoylshikimic acid isomers such as 3-O-caffeoylshikimic acid, 4-O-caffeoylshikimic acid, and 5-O-caffeoylshikimic acid, para-hydroxybenzoic acid (p-hydroxybenzoic acid), protocatechuic acid (PCA), and caffeic acid. Other than shikimic acid, the wsPFBc/OPP may also comprise shikimic acid derivatives.

The wsPFBc/OPP primarily relates to the water-soluble polyphenols such as phenolic acids or compounds and bioactives of oil palm which are derived from the aqueous stream of the palm oil milling process. The aqueous stream of the palm oil milling process is also known as the vegetation liquor is considered as a by-product which is usually discarded. The source of said aqueous stream is from the sterilizer condensate and centrifuge sludge of the palm oil milling process. The sterilization part of the milling process inactivates polyphenol oxidases, while polyphenols such as phenolic acids are bioactive, hence, during the sterilization part, the processed plant compounds undergo changes in function as compared to that of the naturally occurring phenolic acids.

In one embodiment, the water-soluble palm fruit bioactive complex (wsPFBc)/OPP or extracts therefrom or water-soluble polyphenols used in the food and beverage compositions of the present invention may be obtained from vegetation liquor or aqueous stream of palm oil milling.

Vegetation liquor is a by-product of the palm oil milling process which is derived from an aqueous stream which is specifically derived from the sterilizer condensate and centrifuge sludge. While said aqueous stream is often discarded as Palm Oil Milling Effluent (POME) in the whole palm oil milling process, generation of vegetation liquor amounts to 2.5-3.5 $m^3$ for every ton of crude palm oil produced. In the first stage of the palm oil milling process, fresh fruit bunches of the oil palm tree *Elaeis guineensis* are sterilized using high pressure (40 psi) steam (120-140° C.) for better separation of fruit bunches. High pressure steam sterilization further inactivates enzymes that hydrolyze the oil or enzymes that cause fruit deterioration. The high pressure steam further extracts water-soluble components which are then accumulated in the sterilizer condensate. The process then proceeds to the clarification step of palm oil milling to separate the oil from oil-water-sludge emulsion, wherein the oil is then skimmed of while the sedimented fraction (centrifuge sludge) enters the so-called aqueous stream which is rich in water-soluble phenolic acids and other water-soluble non-phenolic phytonutrients as well. The extraction of the whole oil palm vegetation liquor is demonstrated in a published patents U.S. Pat. Nos. 7,387,802B2 and 8,309,145B2, where said vegetation liquor was removed of debris and residual oil using a three-phase high-speed decanter, and then passed through a series of filters to produce a phenolic-enriched filtrate which is the so-called oil palm phenolics (OPP) or water soluble Palm Fruit Bioactive complex (wsPFBc) which contains all polyphenols or plant compounds having notable biological activities. OPP further comprises soluble fibres, sugars, and shikimic acid. In the steaming of said palm oil milling process, it must be noted that the high pressure and high temperature of the steam used inactivates polyphenol oxidases, and activates phenolic acids. While there are few heat-sensitive phenolics which may have been activated, the remaining major phenolic acids that have undergone steaming have been stabilized, improved of their bioavailability, and have their bioactive properties improved (such as antioxidant activities) when compared to their naturally occurring counterparts. While raw, unprocessed, and unextracted phenolic acids and phytonutrients exist in conjugates and complexes with glycosides and proteins, the steaming process modifies the structures and functions of these phenolics which contributes to the improved bioactive properties to which no natural counterpart may be found as similarly performing.

Beverage compositions are liquid compositions that are formulated and prepared for human consumption which may be used to quench thirst, deliver nutrition, or impart health benefits when ingested. Coffee beverages which are derived from coffee bean extracts are major sources of caffeic acid, caffeoylquinic acid, isomers of caffeoylquinic acid. Coffee beverages based on coffee bean extracts have their own unique set of phenolic compounds distinct from wsPFBc/OPP or OPP extracts. Several literatures and studies has reported and confirmed that consumption of caffeoylquinic acid have reported reduced incidence of diabetes, cardiovascular disease, and cancer. Caffeoylquinic acid also comprise anti-inflammatory and antibacterial properties. Cocoa beverages, and tea beverages, which are derived from leaves of different plants, are also comprised of different sets of collective phenolic compounds that impart their own health benefits.

In one embodiment, beverage compositions used in the present invention may include, but not limited to tea beverage compositions, coffee beverage compositions, roasted, and/or cocoa beverage compositions. Said beverage compositions may be in the form of different compositions such as infusion beverage compositions, powder mixes, and/or liquid concentrate mixes. Beverage compositions in liquid forms may be spray dried or freeze dried to obtain compositions in form of a powder. The beverages compositions of the present invention may comprise a combination of wsPFBc/OPP and coffee, wsPFBc/OPP and tea, wsPFBc/OPP and cocoa, or other further combinations. In another embodiment, beverage compositions also include raw materials for the preparation of ready to drink beverages compositions which may include but not limited to roasted coffee beans, roasted coffee grounds, dried tea leaves, crushed or ground tea leaves, roasted cocoa beans, fermented cocoa beans, or cocoa nibs.

In a preferred embodiment, the beverage or beverage composition used in the present invention is a coffee beverage or a coffee beverage composition.

A coffee beverage composition is prepared by a step of roasting raw green coffee beans. Roasting green coffee beans may be roasted in a temperature range of 160-200° C., wherein a light roast, a medium roast, or a dark roast coffee beans is achieved. Roasting green coffee beans in about 6 minutes produces light roast, in about 8 minutes produces medium roast, while in about 11 minutes a dark roast.

Coffee roasting is relevant to the influence in the sensory characteristics of coffee beverages which contribute to the acidity and bitterness. Prolonged roasting time and unequal roasting of individual coffee beans contribute to decrease acidity or intensity of acidity and increase bitterness which lowers coffee quality.

Acidity is one of the attributes that differentiates commodity and specialty coffees. The lack of selection of fruits after harvest favors the mixture of defective and immature seeds, which contributes to the low acidity in commodity coffees. On the other hand, the quality of specialty coffees contributes to better acidity. Acidity also impacts the quality and is one of the attributes evaluated in cupping. The intensity of the perception of acidity increased in both coffees after the addition of wsPFBc, and this may have occurred due to its composition of hydro acids (citric, ascorbic, lactic, glycolic, fumaric, tartaric, and salicylic acids) (U.S. Pat. No. 7,387,802 B2, 2008).

The addition of wsPFBc/OPP of the present invention improves coffee quality of both high quality/high graded or low quality/low graded coffee. In one embodiment, the present invention provides a method of improving the flavor or flavor profile of coffee, particularly improving of improving the flavor or flavor profile of roasted coffee, wherein the roast is light roast, medium roast, or dark roast.

In a preferred embodiment, the addition of wsPFBc/OPP improves the flavor or flavor profile of medium roasted coffee.

Food compositions described herein may include, but not limited to, chocolates, chocolate-based food.

A "commodity coffee" are either raw green coffee beans or roasted coffee beans wherein intrinsic coffee quality is not regarded, graded, or evaluated by a coffee grading association such as the Specialty Coffee Association.

A "specialty coffee", also called specialty grade coffee, is regarded as raw coffee beans or roasted coffee beans to which have positive flavor attributes and profiles which are evaluated and determined by tasting or conducting sensory analysis. Specialty coffee are high quality coffee and have very minute or no defects at all in terms of coffee bean quality and taste profile.

The methods of the present invention preparation of coffee beverages or coffee beverage compositions, the preparations may be in the form of instant coffee mix, instant coffee beverage, brewed coffee, espresso, espresso-based coffee beverages, cold brew, or any related coffee beverage preparation that is known to a person of ordinary skill in the art.

The preparation of coffee beverages or coffee beverage compositions may be provided as ground coffee, granule mix, powder mix, powder concentrates, liquid mix, liquid concentrates, or any related form that is known to a person of ordinary skill in the art.

The present beverage compositions may further include flavour enhancers.

In an embodiment, the caffeoylshikimic acid extracts from water-soluble palm fruit bioactive complex (wsPFBc)/OPP are added and/or mixed with beverages to produce the beverage compositions as disclosed herein. In another embodiment, the isomers of caffeoylshikimic acid, derived from water-soluble palm fruit bioactive complex (wsPFBc)/OPP, are added and/or mixed with the beverages to produce the beverage compositions as disclosed herein. In another embodiment, the OPP extracts including caffeoylshikimic acid are added to instant beverage compositions or mixes such as instant coffee mixes.

The addition of water-soluble palm fruit bioactive complex (wsPFBc)/OPP extracts imparts additional anti-oxidant properties to the coffee or other such beverages. The palm fruit bioactives, caffeoylshikimic acid from oil palm, and caffeoylquinic acid which is a major polyphenol in coffee bean extracts share a similar pathway, and thus when brought together through such compositions as described above, provide synergistic advantages/benefits.

In one embodiment, the compositions and methods of the present invention provides a combination of caffeoylshikimic acid from oil palm and caffeoyquinic acid from coffee which consequentially provide a synergistic effect in the antioxidant activity and health benefits provided by the present invention.

The adding of water-soluble palm fruit bioactive complex (wsPFBc)/OPP to coffee or cocoa or green coffee bean extract or coffee/cocoa beverages improves taste, mouth feel, aroma, reduces bitterness, and provides additional health benefits that prevent or help in regulating major diseases and metabolic disorders such as diabetes mellitus, neurological disorders, Alzheimer's, cancer, and cardiovascular diseases among others.

The beverage composition of the present invention provides a use for modifying or altering the fragrance, taste and/or flavour of food and/or beverages. In one embodiment, the invention provides a use for improving or altering the taste and/or flavour of acidic food and/or beverages. In a preferred embodiment, the invention provides a use for improving the taste of acidic and/or bitter food and/or beverages compositions.

The beverage compositions or coffee compositions provided herein may further comprise sweeteners such as *stevia* or sugar.

In a further embodiment, the beverages also include tea from *Camellia sinensis*, or *ginseng* tea, herbal tea, or a combination thereof.

In humans, bitter receptors (hT2receptorRs) are encoded by 25 different bitter receptor genes. The water-soluble palm fruit bioactive complex (wsPFBc)/OPP serve as bitter receptor antagonists that mask bitterness that is tasted in coffee, tea, or cocoa beverage compositions. Said receptor antagonists found in OPP are phenolics and oligosaccharides. Furthermore, p-hydroxybenzoic acid, an OPP, is a known as a flavor enhancer.

In an embodiment, the water-soluble palm fruit bioactive complex (wsPFBc)/OPP contains glucose, fructose, sucrose and these may further modulate bitter taste in food and/or beverages. OPP is high in potassium which presumably imparts a salty taste and this too could mask the bitterness.

In one embodiment, a method for improving the flavour of a food and/or beverage composition is provided.

In one embodiment, the present invention further provides a method for enhancing flavour profile of beverages further comprising a step of adding extracts from a *Cannabis* plant and/or synthetic cannabinoids which further contributes to the improvement of flavour of beverages. Extracts from *Cannabis* plant may be derived using High Performance Liquid Chromatography (HPLC). Extracts from *Cannabis* plant and/or synthetic cannabinoids elicit health benefits or numerous therapeutic effects which includes, but not limited to antioxidant activity, reduction of inflammation, pain reliever, and anti-proliferative effects. While the use of cannabinoids may be therapeutic, its combination along with caffeoylshikimic acid from oil palm, and caffeoylquinic acid from coffee provides a synergistic effect towards the provision of a beverage composition with health benefits, more particularly a synergistic antioxidant effect when combined in a beverage composition.

Sensory Perception of Commodity and Specialty Coffees

Sensory tests were conducted wherein samples were coded with three digits and presented at random. Approximately 30 ml of each sample was offered to the tasters in 50 ml plastic cups. Participants were instructed to rinse their mouths with water between samples to clean the palate. The samples used, degree of roasting, wsPFBc concentration, and stages of sensory analysis are described in FIG. 1.

Selection of Tasters

Figure 2:
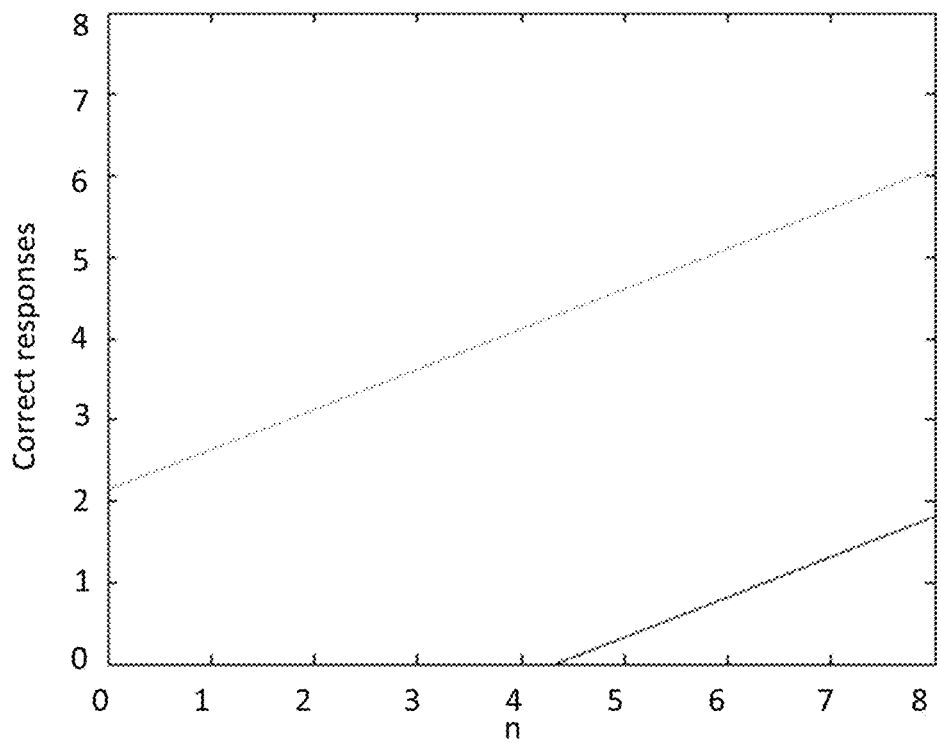
FIG. 2—Screening of taster panel using the Wald graph.

Coffee consumers (20 in number) were invited to participate in the sensory analysis on a voluntary basis. From the triangular test, 7 tasters were selected because they could discriminate samples of commercial coffees with and without the addition of wsPFBc (3%) (Meilgaard, Civille, & Carr, 1999). The results were statistically evaluated using Wald's sequential analysis, according to the graphical method (Amerine, Pangborn, & Roessler, 1965). The Wald graph was constructed based on the parameters P=0·30, pl=0·66, α=0·10, and β=0·05. Further, the judges were selected or rejected according to the number of correct answers (FIG. 2).

In one embodiment, wsPFBc is added in commodity coffee or specialty coffee to produce a beverage composition with enhanced, improved, or modified flavor, that is a coffee beverage composition, wherein said desired beverage composition comprises of about 1-5% wsPFBc/OPP, about 1-4% wsPFBc/OPP, about 1-3% wsPFBc/OPP, about 2-3% wsPFBc/OPP, or about 3% wsPFBc/OPP.

Training Session

The selected tasters were trained to recognize basic tastes that are sweet, sour, and salty, following the recommendations of the Coffee Quality Institute. Three differently tasting solutions with different concentrations were prepared. These were saline (0.1, 0.2, and 0.3%), sweet (0.75, 1.5, and 2.25%), and acidic (0.15, 0.3, and 0.45%). The solutions were presented separately in each session, for the recognition and differentiation of concentrations. After this stage, the solutions were combined in different proportions, and the tasters were asked to identify the basic tastes present in each mixture. The sessions were repeated until all participants were able to discriminate all solutions.

The intensity analysis was conducted after training. The tasters were instructed to taste the coffee samples added with wsPFBc and indicate how much more or less acidic it was than the control (without wsPFBc). The sensory evaluation form was based on a 9 cm unstructured linear scale, anchored at its ends with terms that expressed intensity. When the attribute had the possibility of being equal to the control, the middle of the scale was marked. Besides, they were asked to order the samples according to preference from most preferred to least preferred.

Determination of the Concentration of wsPFBc Added

The sorting task was carried out to group the samples in terms of acidity and determine the best concentrations of PFBc to be added in commodity and specialty coffees. The trained tasters received samples with and without the addition of PFBc in concentrations of 10, 20, 30, 40, and 50 mg/g. Further, they were instructed to group the 12 samples by similarity and describe them according to acidity. The data were subjected to analysis of variance (ANOVA), and the means were compared based on the Scott-Knott test (p<0.05) using the SISVAR software from Ferreira (2014).

In one embodiment, the addition of wsPFBc/OPP in either commodity or specialty coffees may be added in various forms such as dried solids, spray-dried wsPFBc/OPP, freeze-dried wsPFBc/OPP, granules, powders, liquid concentrates, liquids, and other forms known to a person of ordinary skill in the art which may be applied to modification of flavor of beverage compositions. Preferably, the added wsPFBc is in solid form as dried solids, granules, or powders.

Training and Descriptive Analysis of Coffee

Commodity and specialty coffees of the Catuaí red variety processed by the natural (83 and 85 points—SCA scale) and pulped natural (82 and 88 points) methods were subjected to three roasting profiles, namely, light, medium, and dark. The sensory descriptors of the coffees in each roasting profile were defined in a round table testing by three certified Q-grader tasters. The main descriptors included flavors profile and attributes such as citric acid, malic acid, woody, bitter, almonds or nuts, peanuts, caramel, black tea, bitter chocolate, milk chocolate, light-body, heavy-body, spices, phenolic, floral, fruity, yellow fruits, dried fruits, herbaceous, honey, dairy notes, coffee pulp, burnt, rancid, brown sugar, tobacco, and wine. After this stage, the seven tasters were trained to describe the coffee's attributes through the recognition of the described characteristics.

The chosen method with 8% coffee was used to prepare the beverage with and without the addition of PFBc. The concentrations of the bioactive complex were selected according to the taste preferences of commodity and specialty coffees. Further, the sorting task was used to group the 10 coffee samples by similarity and preference and carried out in two sessions for each roasting profile. Additionally, the tasters were instructed to describe the main sensory characteristics of each group. The data were statistically analyzed by employing the Multiple Factor Analysis (MFA) using XLSTAT.

TABLE 1

Sample Identification

| Treatment | Processing | Quality | Light | Medium | Dark |
|---|---|---|---|---|---|
| Control | Natural | Commodity | 611 | 612 | 613 |
|  | Pulped | Specialty (85 pts) | 621 | 622 | 623 |
|  | Natural | Specialty (82 pts) | 631 | 632 | 633 |
|  | Pulped | Specialty (83 pts) | 641 | 642 | 643 |
|  | Natural | Specialty (88 pts) | 651 | 652 | 653 |
|  | Natural | Commodity |  | 667 | 663 |
| PFBc | Natural | Commodity | 411 | 412 | 413 |
|  | Pulped | Specialty (85 pts) | 421 | 472 | 423 |
|  | Natural | Specialty (82 pts) | 431 | 432 | 433 |
|  | Pulped | Specialty (83 pts) | 441 | 442 | 443 |
|  | Natural | Specialty (88 pts) | 451 | 452 | 453 |
|  | Natural | Commodity |  | 462 | 463 |

Selection of wsPFBc Concentration in Coffee

The influence of the addition of the palm fruit bioactive complex (PFBc) on the sensory profile of commodity and specialty coffees was evaluated in this work. The addition of the bioactive complex was shown to influence acidity at different intensities (data not shown) according to the coffee quality. The PFBc concentrations of 30 and 50 mg/g significantly influenced the sample of commodity coffee, and in the sample of specialty coffee, the concentrations of 30, 40, and 50 mg/g showed a significant difference (Table 2). Averages of intensity of acidity were shown in Table 2 and were derived using the Scott-Knott test at 5% probability.

TABLE 2

The intensity of acidity correlated with PFBc concentrations added to coffee

| PFBC (mg/g) | Commodity | Specialty |
|---|---|---|
| 10 | $5.04^b$ | $5.64^b$ |
| 70 | $5.72^b$ | $5.62^b$ |
| 30 | $6.05^a$ | $6.69^a$ |
| 40 | $5.3^b$ | $6.49^a$ |
| 50 | $6.87^a$ | $6.56^a$ |

Figure 4:
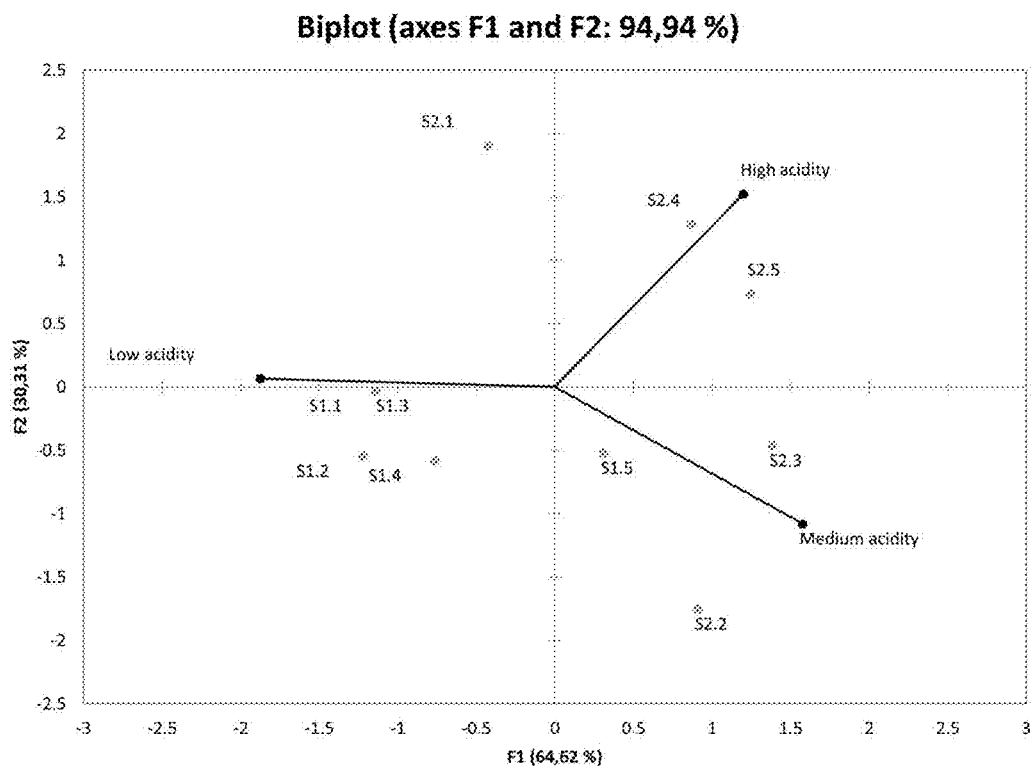
FIG. 4—Sensory characteristics of commodity (S1) and specialty (S2) coffees with wsPFBc added. 1 (10 mg/g), 2 (20 mg/g), 3 (30 mg/g), 4 (40 mg/g), 5 (50 mg/g), and 6 (control).

From the preference analysis, the concentrations of 30 mg/g and 40 mg/g were selected for commodity and specialty coffees, respectively (FIG. 3.1). In these concentrations, the addition of wsPFBc increased the acidity of the drinks. Commodity coffee had low acidity, whereas specialty coffees had a high acidity (FIG. 4). Furthermore, the addition of 40 mg/g of wsPFBc on the sensory profile of *Arabica* coffees showed an excellent perception of sweetness, acidity, aftertaste, and less astringency (FIG. 3.2). Noticeable floral and spice notes were observed in 20 mg/g and 40 mg/g wsPFBc added *Arabica* coffee while fruity and sour/fermented notes were perceived more intensely at the concentration of 40 mg/g (FIG. 3.3). It is further emphasized that the enhancement and modification of the coffee beverages using wsPFBc has increased perception of sweetness, which is contrary to the common improvement of flavor by addition of sugar components which only increases sugar content which is a major problem for consumers that have compromised health, particularly coffee drinkers which body and digestion that is not able to process sugars.

In FIG. 3.1 where different commodity and specialty coffees, which were added with wsPFBc, were scored and graded by the standardized coffee tasters or coffee Q-graders following the Specialty Coffee Association protocols and methodologies for grading coffee. The addition of 40 mg/g of wsPFBc in specialty (S2) coffee was the most preferred (preference A) while the addition of 10 mg/g and 30 mg/in commodity coffee (S1) was the next most preferred (preference B).

In FIG. 4 where sensory characteristics were assessed, specialty coffees (S2) with 40 mg/g and 50 mg/g added wsPFBc were determined to have high acidity while commodity coffee (S1) with added 10 mg/g and 30 mg/g were determined to have low acidity.

Acidity is important in the overall quality of the coffee with consequently affects evaluation during coffee cupping, as well as perception of acidity. While commodity coffee are often classified as low quality due to their loss of acidity, the primary cause may be pointed to lack of quality fruit selection after harvest, lack of selection of mature seeds, and lack of quality control in removing defective seeds. In these cases, the perception of acidity, as well as the acidity of coffee is not given well by commodity coffee. The increase in the perception of acidity for both commodity and specialty coffee may have been due to the composition of the added wsPFBc which comprises organic acids such as citric acid, ascorbic acid, lactic acid, glycolic acid, fumaric acid, tartaric acid, and salicylic acid.

Gas Chromatography-Mass Spectrometry (GC-MS) Analysis

The analysis of volatile compounds was performed in commodity and specialty coffees medium roasting at the following concentrations of PFBc: 0, 10, 20, 30, 40, and 50 mg/g. The volatile compounds of the PFBc matrix were also evaluated. Volatile compounds were extracted using manual Headspace-solid phase microextraction (HS-SPME) from coffee beverages. The compounds were analyzed using a Shimadzu QP2010 GC model equipped with mass spectrometry (MS) and a silica capillary Carbo-Wax 20M (30 m×0.25 mm×0.25 mm) column. The oven temperature was maintained at 60° C. for 5 min with increments of 10° C./min and then maintained at 230° C. for 15 min. Injector temperatures were kept at 230° C. in splitless mode. The volatile compounds were identified by comparing the mass spectra to the NIST11 library. 9

Also, an alkane series (C10-C40) was used to calculate the retention index (RI) for each compound and compare it with RI values found in the literature.

Commodity and specialty coffee samples submitted to GC-MS analysis differed in terms of volatile composition. From the 88 identified compounds, there were 13 acids, 8 alcohol, 2 aldehyde, 1 amide, 3 esters, 10 furans, 3 ketones, 2 lactones, 6 phenol, 2 pyranones, 2 pyrazines, 1 pyridine, and 34 others (Table 2).

TABLE 2

Volatile compound (area) of commodity and specialty coffees with wsPFBc added in different concentrations.

| Compounds | RI | PFBC | Commodity PFBc concentration (area) | | | | | |
| --- | --- | --- | --- | --- | --- | --- | --- | --- |
| | | | 0 | 10 | 20 | 30 | 40 | 50 |
| Acid | | | | | | | | |
| Propanoic Acid | 1518 | 1300064 | 11 | 37 | 34 | 27 | 19 | 41 |
| 2-Butenoic Acid | 1776 | 0 | 41 | 78 | 68 | 77 | 77 | 106 |
| 3-methyl-2-Pyridine-carboxylic acid methyl ester | 1885 | 245 | 0 | 0 | 0 | 0 | 0 | 0 |
| Acetic acid | 1431 | 0 | 2418432 | 4273600 | 3867183 | 2854023 | 2733202 | 3216481 |
| Butanoic acid | 1651 | 201 | 338 | 666 | 612 | 519 | 470 | 920 |
| 3-methyl-Cyclohexane-carboxylic acid | 1995 | 161 | 0 | 0 | 0 | 0 | 0 | 0 |
| Hexadecanoic acid methyl ester | 2107 | 24 | 18 | 28 | 114 | 44 | 63 | 26 |
| Hexanoic acid | 1816 | 1194638 | 0 | 85 | 72 | 75 | 85 | 134 |
| Decanoic acid | 2171 | 74 | 0 | 0 | 0 | 0 | 0 | 0 |
| Nonanoic acid | 2067 | 117 | 21 | 48 | 46 | 27 | 45 | 56 |
| Octanoic acid | 1958 | 218 | 11 | 28 | 30 | 24 | 44 | 48 |
| Pentanoic acid | 1723 | 3455426 | 7 | 34 | 24 | 22 | 28 | 41 |
| 4-hydroxyphenyl phosphonic acid | 1895 | 822 | 1645697 | 2380356 | 2363977 | 2059550 | 1557951 | 2521381 |
| Alcohol | | | | | | | | |
| 1-Dodecanol | 1882 | 110 | 365 | 96 | 986 | 257 | 149 | 67 |
| 4-Nonanol | 1476 | 8753431 | 0 | 0 | 0 | 0 | 0 | 0 |
| Benzyl alcohol | 1831 | 116 | 99 | 26 | 26 | 27 | 21 | 109 |
| 2-(dodecyloxy)-Ethanol | 2142 | 0 | 25 | 26 | 110 | 52 | 52 | 26 |
| 1-Heptadecanol | 2267 | 141 | 175 | 54 | 66 | 122 | 273 | 86 |
| 1-Heptadecanol | 2268 | 141 | 175 | 54 | 65 | 122 | 273 | 86 |
| 1-Tridecanol | 2073 | 9 | 12 | 10 | 70 | 29 | 30 | 11 |
| Phenylethyl Alcohol | 1851 | 139 | 186 | 224 | 212 | 237 | 178 | 503 |
| Aldehyde | | | | | | | | |

TABLE 2-continued

Volatile compound (area) of commodity and specialty coffees with wsPFBc added in different concentrations.

| | | | | | | | | |
|---|---|---|---|---|---|---|---|---|
| Benzene-acetaldehyde.alpha.-ethylidene- | 1861 | 14 | 128 | 167 | 168 | 145 | 124 | 192 |
| 2-Furancarbox-aldehyde 5-methyl-Amide | 1543 | 102 | 8185084 | 13221919 | 13145821 | 9541586 | 7937607 | 11839760 |
| Acetamide | 1788 | 414 | 0 | 0 | 0 | 0 | 0 | 0 |
| Ester | | | | | | | | |
| Dibutyl adipate | 2162 | 178 | 25 | 124 | 91 | 34 | 94 | 20 |
| Homosalate | 2337 | 26 | 14 | 21 | 75 | 47 | 82 | 37 |
| Isopropyl palmitate | 2132 | 39 | 24 | 16 | 21 | 24 | 37 | 20 |
| Furan | | | | | | | | |
| 2-Furanmethanol | 1632 | 902 | 7137434 | 9788869 | 9281580 | 8384452 | 6592188 | 9691290 |
| 2-Furanmethanol acetate | 1495 | 0 | 12113563 | 16684506 | 17485390 | 11834990 | 10242856 | 6554472 |
| 2-Furanmethanol propanoate | 1558 | 8 | 1686123 | 1639499 | 1816336 | 1421244 | 1136969 | 608 |
| Benzofuran 23-dihydro- | 2286 | 24 | 191 | 205 | 234 | 266 | 219 | 288 |
| Ethanone 1-(1H-pyrrol-2-yl)- | 1882 | 129 | 955 | 1016797 | 978 | 1199602 | 893 | 1151084 |
| Ethanone 1-(2-furanyl)- | 1471 | 0 | 2147256 | 2507625 | 3335160 | 2370280 | 2055874 | 3055097 |
| Furan 22'-[oxybis(methylene)]bis- | 1878 | 0 | 2128791 | 2533889 | 2795157 | 2452389 | 2059073 | 3102941 |
| Furan 22'-methylenebis- | 1562 | 74 | 1218749 | 378 | 419 | 213 | 296 | 333 |
| Furan 22'-[(methylthio)methyl]- | 1442 | 52 | 1897181 | 1059051 | 645 | 889 | 790 | 566 |
| Furfural | 1417 | 254 | 5678822 | 2519730 | 8286589 | 2075151 | 1354555 | 9162216 |
| Ketone | | | | | | | | |
| 2-Propanone 1-(acetyloxy)- | 1427 | 0 | 2315066 | 4154653 | 3762138 | 3106031 | 2643767 | 3042131 |
| 4-Hydroxy-2-methyl-acetophenone | 2091 | 157 | 6995429 | 8220536 | 8785776 | 7951264 | 6542514 | 9939825 |
| 2.5-Dimethyl-4-hydroxy-3(2H)-furanone | 1950 | 353 | 48 | 41 | 84 | 60 | 86 | 86 |
| Lactone | | | | | | | | |
| δ-Valerolactone | 1803 | 210 | 0 | 0 | 0 | 0 | 0 | 0 |
| Dehydrome valonic lactone | 1945 | 127 | 0 | 0 | 0 | 0 | 0 | 0 |
| Phenol | | | | | | | | |
| Phenol 24-bis (11-dimethylethyl)- | 2188 | 463 | 144 | 135 | 192 | 161 | 208 | 236 |
| Phenol | 1895 | 822 | 1665783 | 2380356 | 2363977 | 2059550 | 1557951 | 2521381 |
| Phenol 2-methoxy- | 1818 | 28 | 2887870 | 4397541 | 4311312 | 3441795 | 2720909 | 4463501 |
| Phenol 3-methyl- | 1982 | 6 | 159 | 213 | 209 | 195 | 144 | 252 |
| Phenol 4-ethyl- | 2070 | 7 | 253 | 329 | 322 | 312 | 247 | 417 |
| Phenol 4 ethyl-2-methoxy- | 1914 | 47 | 5580342 | 7365718 | 7364182 | 6613943 | 5395609 | 8765283 |
| Pyranone | | | | | | | | |
| 2.3-dihydro-3.5-dihydroxy-6-methyl-4H-pyran-4-one | 2177 | 946 | 0 | 106 | 28 | 0 | 0 | 0 |
| Maltol | 1889 | 1226903 | 275 | 487 | 319 | 384 | 302 | 263 |

TABLE 2-continued

Volatile compound (area) of commodity and specialty coffees with wsPFBc added in different concentrations.

| Pyrazine | | | | | | | | |
|---|---|---|---|---|---|---|---|---|
| Pyrazine 2-ethyl-3.5-dimethyl- | 1458 | 0 | 1414304 | 2099077 | 745 | 1621287 | 1396079 | 2185738 |
| Pyrazine trimethyl- | 1398 | 0 | 771 | 1773963 | 1692734 | 1203565 | 1049909 | 1674772 |
| Pyridine 4(H)- | 1684 | 16 | 1015820 | 1386852 | 1430313 | 1168499 | 977 | 1475792 |
| Pyridine N-acetyl- | | | | | | | | |
| Others | | | | | | | | |
| 355-Trimethylhexyl acetate | 1369 | 601 | 0 | 0 | 0 | 0 | 0 | 0 |
| 13-Dioxol-2-one 4.5-dimethyl- | 2043 | 1688264 | 16 | 50 | 28 | 17 | 11 | 34 |
| 16-Octadien-3-ol 37-dimethyl- | 1532 | 0 | 125 | 100 | 88 | 74 | 58 | 66 |
| 1H-Pyrrole-2-carboxaldehyde 1-methyl- | 1588 | 132 | 1882213 | 3056925 | 3103782 | 2006887 | 1720801 | 2527405 |
| 2-Thiophene methanol | 1865 | 0 | 50 | 59 | 54 | 60 | 48 | 65 |
| Furfural acetone | 1846 | 0 | 98 | 126 | 155 | 135 | 102 | 181 |
| 3-Furanacetic acid 4-hexyl-2.5-dihydro-2.5-dioxo- | 2006 | 197 | 0 | 22 | 15 | 4 | 19 | 50 |
| 4-Hydroxy-3-methyl-acetophenone | 1905 | 5 | 181 | 227 | 272 | 241 | 199 | 314 |
| 23-Bis(acetyloxy) butanedioic acid | 1428 | 0 | 2353860 | 4154653 | 3773185 | 3116110 | 2664510 | 3102614 |
| Megastigmatrienone | 2125 | 0 | 15 | 17 | 20 | 17 | 16 | 22 |
| Octyl ether | 1743 | 42 | | 0 | 0 | 0 | 0 | 0 |
| Oxazolidine 220-diethyl-3-methyl- | 1829 | 86 | 0 | 0 | 0 | 0 | 0 | 0 |
| RT:11.735 | 1650 | 601 | 0 | 0 | 0 | 0 | 0 | 0 |
| RT:11.940 | 1668 | 0 | 483 | 803 | 796 | 558 | 505 | 912 |
| RT:12.405 | 1706 | 0 | 1250931 | 502 | 533 | 409 | 348 | 379 |
| RT:12:435 | 1709 | 0 | 421 | 589 | 577 | 452 | 356 | 579 |
| RT:13.435 | 1792 | 1351502 | 1472823 | 803 | 1573863 | 698 | 861 | 1097519 |
| RT:13.495 | 1797 | 1351502 | 1555220 | 841 | 1626025 | 698 | 861 | 1097519 |
| RT:13.945 | 1820 | 17 | 791 | 1018073 | 1079509 | 954 | 803 | 1292403 |
| RT:14.230 | 1834 | 3 | 1597193 | 915 | 908 | 819 | 610 | 650 |
| RT:14.785 | 1862 | 0 | 170 | 234 | 224 | 184 | 148 | 228 |
| RT:14.980 | 1871 | 0 | 266 | 306 | 363 | 316 | 227 | 450 |
| RT:15.015 | 1873 | 66 | 0 | 0 | 0 | 0 | 0 | 0 |
| RT:15.135 | 1879 | 294 | 0 | 0 | 0 | 0 | 0 | 0 |
| RT:15.325 | 1888 | 173 | 333 | 273 | 441 | 185 | 607 | 1843245 |
| RT:16.205 | 1968 | 109 | 0 | 0 | 0 | 0 | 0 | 0 |
| RT:16.650 | 2016 | 64 | 0 | 0 | 0 | 0 | 0 | 0 |
| RT:16.990 | 2053 | 22 | 56 | 55 | 60 | 35 | 198 | 475 |
| RT:17.495 | 2107 | 24 | 0 | 0 | 0 | 0 | 0 | 0 |
| RT:17.885 | 2149 | 90 | 0 | 0 | 0 | 0 | 0 | 0 |
| RT:17.890 | 2149 | 90 | 557 | 659 | 744 | 717 | 579 | 922 |
| RT:18.105 | 2172 | 0 | 113 | 157 | 173 | 184 | 135 | 230 |
| RT:22.860 | 2683 | 17 | 2 | 8 | 13 | 6 | 9 | 3 |
| Trisiloxane 1.1.1.5.5.5-hexamethyl-3.3-bis[(trimethylsilyl)oxy]- | 1616 | 527 | 512 | 127 | 1013566 | 480 | 156 | 157 |

TABLE 2-continued

Volatile compound (area) of commodity and specialty coffees with wsPFBc added in different concentrations.

| Compounds | Specialty PFBc concentration (area) | | | | | |
|---|---|---|---|---|---|---|
| | 0 | 10 | 20 | 30 | 40 | 50 |
| Acid | | | | | | |
| Propanoic Acid | 49 | 35 | 27 | 43 | 37 | 36 |
| 2-Butenoic Acid | 167 | 139 | 114 | 154 | 186 | 210 |
| 3-methyl-2-Pyridinecarboxylic acid methyl ester | 0 | 0 | 0 | 0 | 0 | 0 |
| Acetic acid | 2768503 | 1843518 | 1497918 | 2597118 | 2456190 | 1996276 |
| Butanoic acid | 1199352 | 1146323 | 1154580 | 1180351 | 1368455 | 1643821 |
| 3-methyl-Cyclohexane-carboxylic acid | 0 | 0 | 0 | 0 | 0 | 0 |
| Hexadecanoic acid methyl ester | 33 | 34 | 36 | 37 | 37 | 55 |
| Hexanoic acid | 125 | 100 | 91 | 132 | 150 | 217 |
| Decanoic acid | 0 | 0 | 0 | 0 | 0 | 0 |
| Nonanoic acid | 59 | 41 | 42 | 51 | 44 | 76 |
| Octanoic acid | 44 | 22 | 31 | 35 | 23 | 61 |
| Pentanoic acid | 21 | 21 | 24 | 45 | 48 | 76 |
| 4-hydroxyphenyl phosphonic acid | 270 | 227 | 208 | 239 | 278 | 352 |
| Alcohol | | | | | | |
| 1-Dodecanol | 97 | 62 | 90 | 89 | 86 | 111 |
| 4-Nonanol | 2957810 | 853 | 119 | 553 | 1764725 | 901 |
| Benzyl alcohol | 44 | 36 | 28 | 39 | 49 | 60 |
| 2-(dodecyloxy)-Ethanol | 20 | 18 | 33 | 21 | 21 | 33 |
| 1-Heptadecanol | 48 | 35 | 34 | 39 | 32 | 34 |
| 1-Heptadecanol | 48 | 35 | 34 | 36 | 32 | 34 |
| 1-Tridecanol | 21 | 16 | 24 | 18 | 15 | 21 |
| Phenylethyl Alcohol | 281 | 198 | 146 | 218 | 258 | 341 |
| Aldehyde | | | | | | |
| Benzeneacet-aldehyde.alpha.-ethylidene- | 108 | 83 | 85 | 91 | 117 | 157 |
| 2-Furancarbox-aldehyde 5-methyl- | 9829899 | 9145793 | 10953642 | 9282604 | 11086572 | 13602906 |
| Amide | | | | | | |
| Acetamide | 0 | 0 | 0 | 0 | 0 | 0 |
| Ester | | | | | | |
| Dibutyl adipate | 100 | 701 | 353 | 487 | 493 | 576 |
| Homosalate | 48 | 59 | 58 | 54 | 56 | 65 |
| Isopropyl palmitate | 15 | 9 | 7 | 10 | 10 | 11 |
| Furan | | | | | | |
| 2-Furanmethanol | 5393720 | 4727051 | 4387766 | 4757822 | 4987850 | 5391194 |
| 2-Furanmethanol acetate | 3548068 | 3462977 | 4640233 | 3566608 | 4047144 | 4561224 |
| 2-Furanmethanol propanoate | 219 | 261 | 351 | 224 | 258 | 291 |
| Benzofuran 23-dihydro- | 136 | 102 | 77 | 107 | 142 | 184 |
| Ethanol 1-(1H-pyrrol-2-yl)- | 540 | 390 | 257 | 418 | 485 | 556 |
| Ethanone 1-(2-furanyl)- | 2516256 | 2380389 | 3214509 | 2410837 | 2670549 | 2737259 |
| Furan 22'-[oxybis(methylene)]bis- | 310 | 239 | 259 | 248 | 352 | 438 |
| Furan 22'-methylenebis- | 24 | 29 | 37 | 27 | 48 | 15 |
| Furan 2-[(methylthio)methyl]- | 0 | 0 | 0 | 0 | 0 | 0 |
| Furfural | 12303618 | 6325074 | 11872886 | 12711619 | 1471808 | 11797534 |

TABLE 2-continued

Volatile compound (area) of commodity and specialty coffees with wsPFBc added in different concentrations.

| Ketone | | | | | | |
|---|---|---|---|---|---|---|
| 2-Propanone 1-(acetyloxy) | 1990024 | 1815768 | 1492676 | 2083044 | 1624237 | 1717211 |
| 4-Hydroxy-2-methylacetophenone | 2468047 | 1891763 | 1720490 | 1947355 | 2573375 | 3353271 |
| 2.5-Dimethyl-4-hydroxy-3(2H)-furanone | 103 | 65 | 20 | 78 | 72 | 53 |
| | | | 0 | 0 | 0 | 0 |
| Lactone | | | | | | |
| δ-Valerolactone | 0 | 0 | 0 | 0 | 0 | 0 |
| Dehydromevalonic lactone | 0 | 0 | 0 | 0 | 0 | 0 |
| Phenol | | | | | | |
| Phenol 24-bis (11-dimethylethyl)- | 101 | 110 | 147 | 136 | 320 | 272 |
| Phenol | 270 | 227 | 208 | 239 | 278 | 352 |
| Phenol 2-methoxy- | 305 | 251 | 263 | 264 | 316 | 411 |
| Phenol 3-methyl- | 60 | 45 | 39 | 47 | 59 | 79 |
| Phenol 4-ethyl- | 44 | 32 | 29 | 35 | 46 | 60 |
| Phenol 4-ethyl-2-methoxy- | 347 | 264 | 260 | 269 | 348 | 476 |
| Pyranone | | | | | | |
| 2.3-dihydro-3.5-dihydroxy-6-methyl-4H-pyran-4-one | 60 | 47 | 11 | 39 | 35 | 31 |
| Maltol | 176 | 131 | 64 | 144 | 151 | 134 |
| Pyrazine | | | | | | |
| Pyrazine 2-ethyl-3.5-dimethyl- | 733 | 638 | 676 | 645 | 800 | 1181131 |
| Pyrazine trimethyl- | 602 | 453 | 524 | 549 | 243 | 429 |
| Pyridine 4(H)- | 577 | 457 | 415 | 481 | 556 | 680 |
| Pyridine N-acetyl- | | | | | | |
| Others | | | | | | |
| 355-Trimethylhexyl acetate | 0 | 0 | 0 | 0 | 0 | 0 |
| 13-Dioxol-2-one 4.5-dimethyl- | 29 | 27 | 21 | 10 | 23 | 32 |
| 16-Octadien-3-ol 37-dimethyl- | 74 | 64 | 94 | 75 | 97 | 97 |
| 1H-Pyrrole-2-carboxaldehyde 1-methyl- | 1330085 | 1220831 | 1539980 | 1237550 | 1428869 | 1781596 |
| 2-Thiophene-methanol | 45 | 31 | 21 | 34 | 40 | 44 |
| Furfural acetone | 57 | 43 | 45 | 48 | 67 | 88 |
| 3-Furanacetic acid | 0 | 7 | 15 | 33 | 48 | 72 |
| 4-hexyl-2.5-dihydro-2.5-dioxo- | 68 | 56 | 54 | 58 | 77 | 109 |
| 4-Hydroxy-3-methylacetophenone | | | | | | |
| 23-Bis(acetyloxy) butanedioicacid | 1944531 | 1825883 | 1497918 | 897 | 2384873 | 1959941 |
| Megastigmatrienone | 13 | 11 | 10 | 10 | 14 | 18 |
| Octyl ether | 0 | 0 | 0 | 0 | 0 | 0 |
| Oxazolidine 220-diethyl-3-methyl- | 0 | 0 | 0 | 0 | 0 | 0 |
| RT:11.735 | 0 | 0 | 0 | 0 | 0 | 0 |
| RT:11.940 | 217 | 167 | 165 | 182 | 201 | 294 |
| RT:12.405 | 259 | 231 | 366 | 290 | 379 | 236 |
| RT:12.435 | 45 | 46 | 47 | 42 | 56 | 72 |
| RT:13.435 | 221 | 132 | 153 | 100 | 179 | 268 |
| RT:13.495 | 239 | 132 | 153 | 100 | 178 | 265 |
| RT:13.945 | 619 | 473 | 407 | 507 | 644 | 914 |
| RT:14.230 | 197 | 141 | 174 | 155 | 185 | 130 |
| RT:14.785 | 0 | 0 | 0 | 0 | 0 | 0 |

TABLE 2-continued

Volatile compound (area) of commodity and specialty coffees with wsPFBc added in different concentrations.

| | | | | | | |
|---|---|---|---|---|---|---|
| RT:14.980 | 167 | 128 | 118 | 137 | 171 | 257 |
| RT:15.015 | 0 | 0 | 0 | 0 | 0 | 0 |
| RT:15.135 | 0 | 0 | 0 | 0 | 0 | 0 |
| RT:15.325 | 48 | 29 | 42 | 29 | 54 | 158 |
| RT:16.205 | 0 | 0 | 0 | 0 | 0 | 0 |
| RT:16.650 | 0 | 0 | 0 | 0 | 0 | 0 |
| RT:16.990 | 19 | 14 | 17 | 14 | 19 | 127 |
| RT:17.495 | 0 | 0 | 0 | 0 | 0 | 0 |
| RT:17.885 | 0 | 0 | 0 | 0 | 0 | 0 |
| RT:17.890 | 529 | 407 | 367 | 427 | 566 | 754 |
| RT:18.105 | 127 | 125 | 127 | 120 | 137 | 186 |
| RT:22.860 | 3 | 16 | 12 | 13 | 17 | 23 |
| Trisiloxane 1.1.1.5.5.5-hexamethyl-3.3-bis[(trimethylsilyl)oxy]- | 244 | 79 | 82 | 65 | 101 | 189 |

2-Pyridinecarboxylic acid methyl ester; decanoic acid; acetamide; δ-valerolactone; dehydromevalonic lactone; 3,5,5-trimethylhexyl acetate; octyl ether; oxazolidine 2,2-diethyl-3-methyl-; among other non-identified volatiles (RT: 11.735; RT: 11.940; RT: 12.405; RT: 12.435; RT: 13.435; RT: 13.495; RT: 13.945; RT: 14.230; RT: 14.785; RT: 14.980; RT: 15.015; RT: 15.135; RT: 15.325; RT: 16.205; RT: 16.650; RT: 16.990; RT: 17.495; and RT: 17.885) were present in the Palm Fruit Bioactive complex (PFBc), However, these compounds were not detected after coffee preparation. Volatile compounds that have low molecular weight (<300 Da) which characterizes them by the rapid volatilization and were probably volatilized during the coffee extraction process.

The principal component analysis explained 74.63% of the variation in data for commodity coffee and 71.87% of the variation in specialty coffee variation. The coffees without PFBc were grouped separately from the others, showing the influence of PFBc on the volatiles profile (S1.0 and S2.0).

Ester was the group of volatiles correlated with commodity coffee added with 30 mg/g of PFBC (S1.3) represented by dibutyl adipate, homosalate, and isopropyl palmitate.

In one embodiment, the beverage composition with added wsPFBc of the present invention, particularly commodity coffee beverage compositions or commodity coffee, further comprises of volatile compounds, wherein said volatile compounds are esters selected from the group consisting of dibutyl adipate, homosalate, and isopropyl palmitate.

Specialty coffee with 40 mg/g of PFBc (S2.4) was correlated with acids and pyranone. Propanoic acid; 2-butenoic acid 3-methyl-; acetic acid; butanoic acid 3-methyl-; hexadecanoic acid methyl ester; hexanoic acid; decanoic acid; nonanoic acid; octanoic acid; pentanoic acid; and 4-hydroxybenzenephosphonic acid were present in coffee, and their concentration has changed with the addition of PFBc. High acidity was noticeable by the tasters and was probably influenced by the intensity of the volatile acids. Acetic acid, butanoic acid, and hexanoic acid have been reported as the main volatile acids that influence coffee acidity. Propanoic acid causes off-flavor to the coffee beverage and addition of wsPFBc in coffee reduced propanoic acid content by 24.8% when compared with coffee without wsPFBc.

In one embodiment, the beverage composition with added wsPFBc of the present invention, particularly specialty coffee beverage compositions or specialty coffee, further comprises of acids and pyranone, selected from the group consisting of propanoic acid; 2-butenoic acid 3-methyl-; acetic acid; butanoic acid 3-methyl-; hexadecanoic acid methyl ester; hexanoic acid; decanoic acid; nonanoic acid; octanoic acid; pentanoic acid; and 4-hydroxybenzenephosphonic acid.

The medium-chain fatty acids such as nonanoic acid, octanoic acid, decanoic acid, and pentanoic acid contribute to the overall volatile profiles, conferring on them moderate and pleasant notes.

Pyranones are generated from sugar fragmentation of deoxyosones, resulting in 2,3-dihydro-3,5-dihydroxy-6-methyl-4H-pyran-4-one, and maltol imparting a caramel aroma to the beverage can contribute to antioxidant capacity.

Influence of wsPFBc on Coffees of Different Qualities

Figure 5:
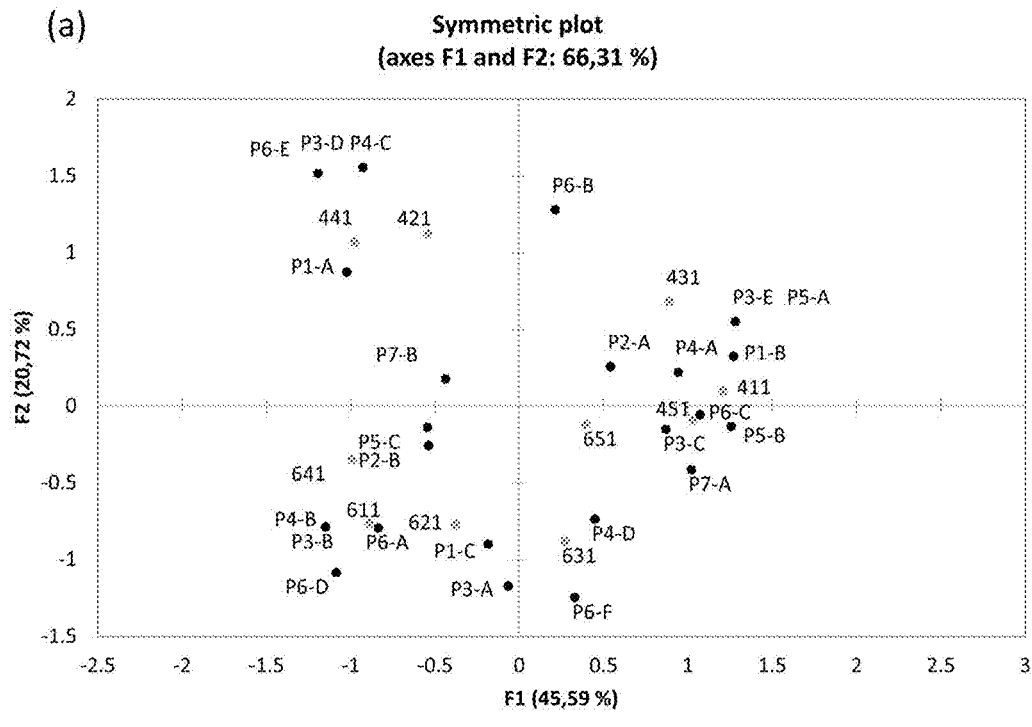
FIGS. 5a-5c—Similarity between commodity and specialty coffees in light (a), medium (b), and dark (c) roasts.
Figure 5:
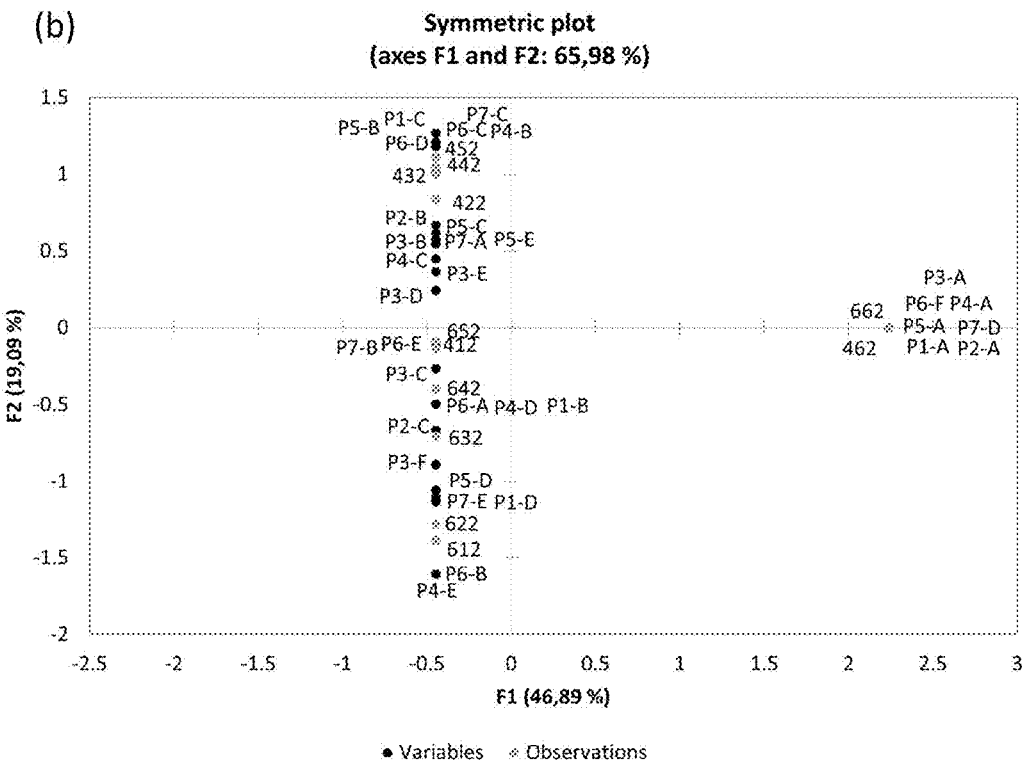
Figure 5:
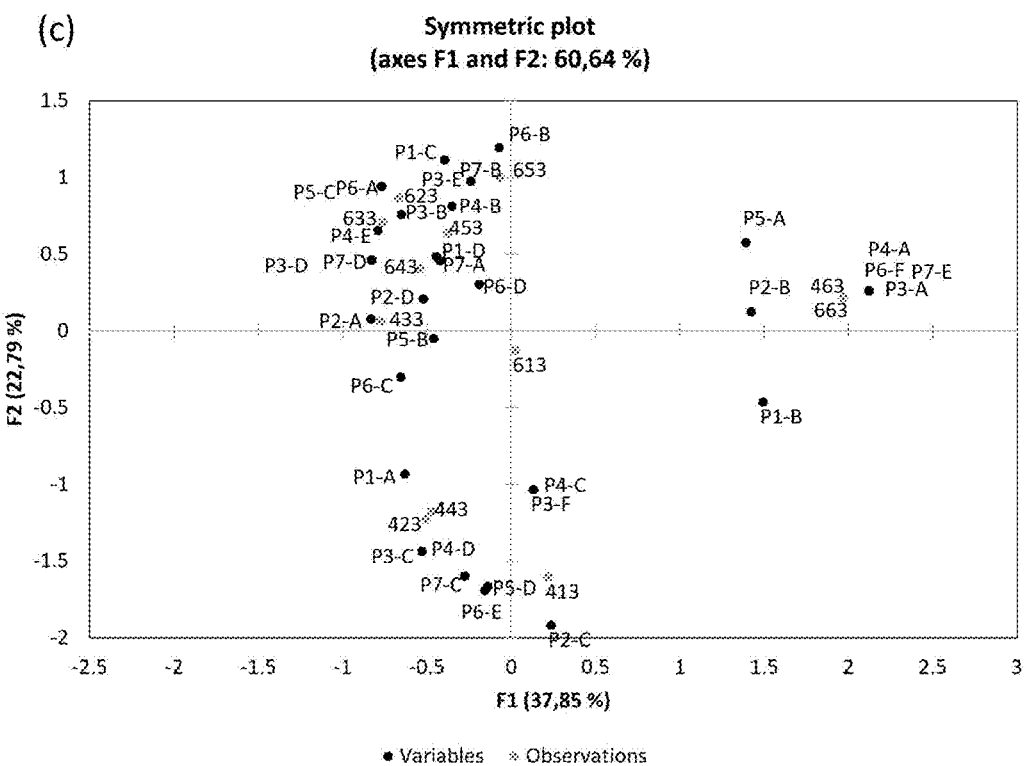

The bioactive complex of palm fruit extract is rich in phenolic compounds that, in addition to having antioxidant properties, are characterized as aromatic metabolites, contributing to changes in the sensory profile of the final product. The perception of PFBc in the coffee was evident in the medium roasted variants, followed by light and dark roasted coffees. At each stage of the roasting process, the sensory characteristics of coffee beans were modified due to changes in the concentrations of volatile and non-volatile compounds present in the beans. In the light roast (FIG. 5), natural coffee classified at 88 points was the type one that showed no difference in sensory characteristics after the addition of wsPFBc and was grouped in the negative component (F2).

Figure 6:
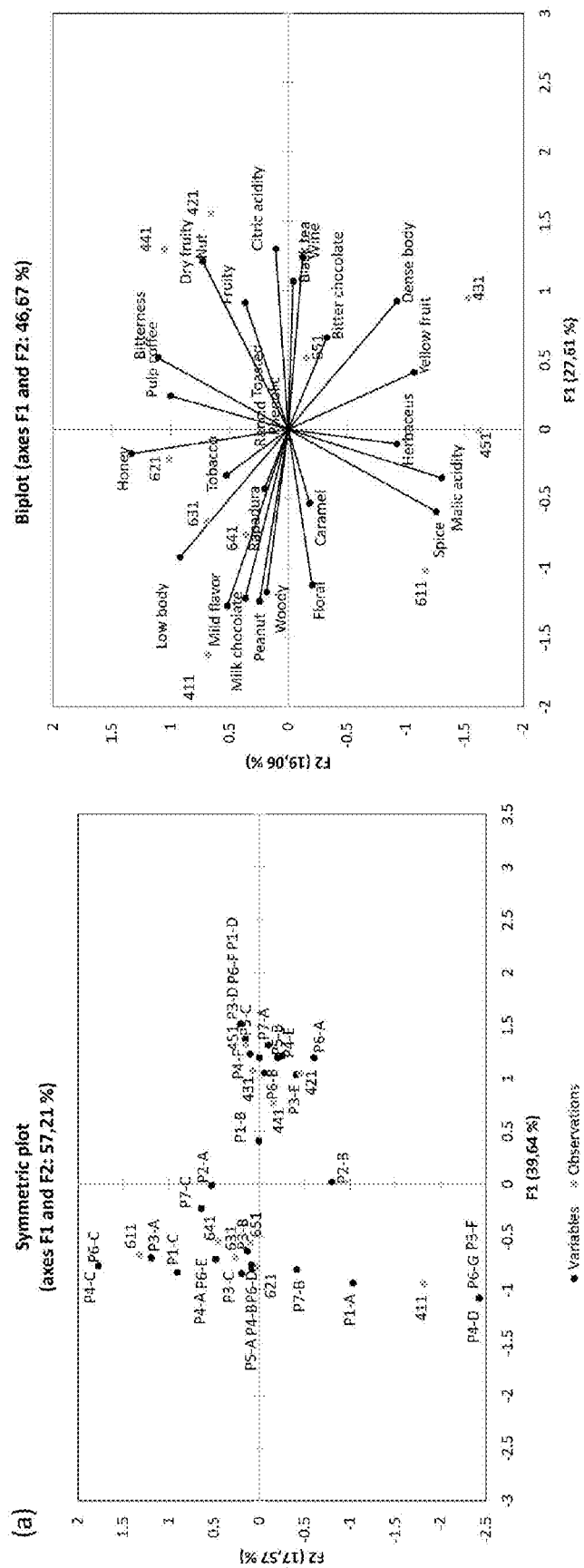
FIGS. 6a-6c—Preference and characterization of commodity and specialty coffees after light (a), medium (b), and dark (c) roasting.
Figure 6:
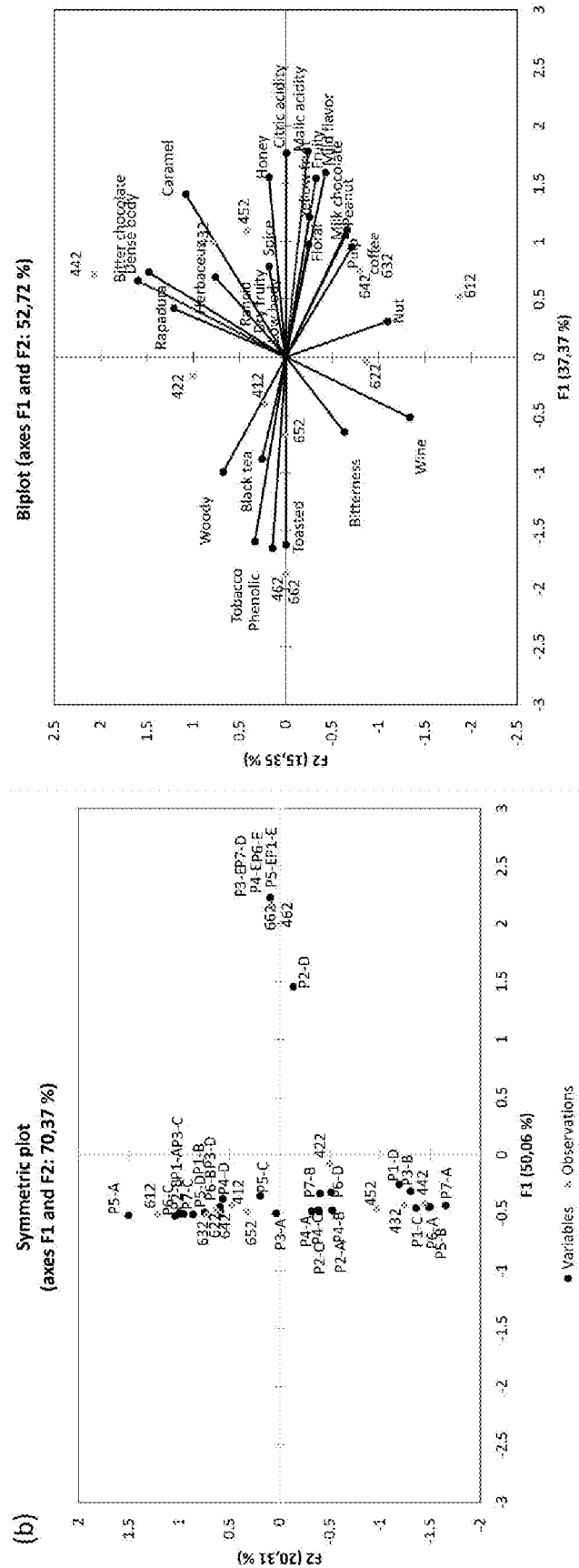
Figure 6:
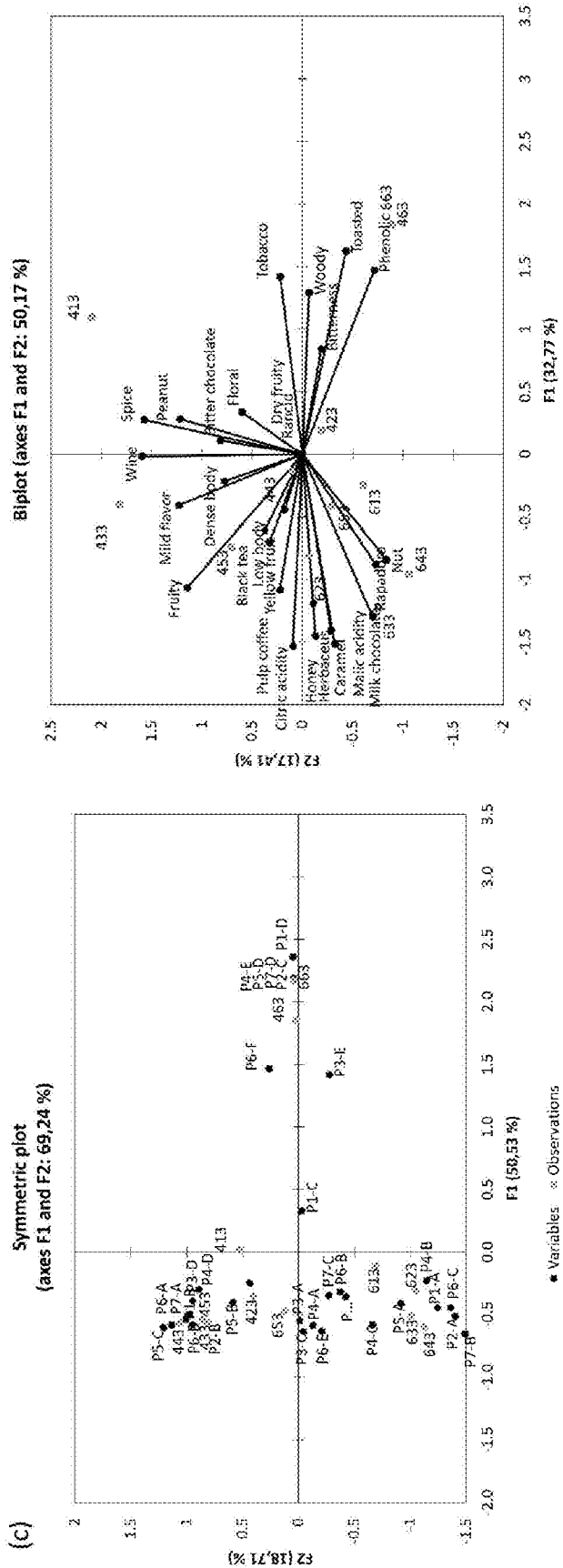

Among the roasting profiles, FIG. 6 shows the preferences and characterization of the coffee roast profiles under light roast (6a), medium roast (6b), and dark roast (6c). The medium roast is considered ideal because it has a balance between flavor and aroma, contributing to a full beverage with an intense citrus flavor compared to other roasts according to literatures. In this roasting profile, specialty coffees with scores below 85, such as coffees processed by the natural (82 pts) and pulped (83 pts) methods, showed greater acceptance after the addition of wsPFBc. Despite being classified as "very good" coffees (80-84.99), the reduced complexity of aroma and flavor when compared to coffees with higher scores allowed a better performance of wsPFBc, contributing to an increase in the body.

The addition of wsPFBc was less noticeable in coffee with a dark roast. Control pulped (83 and 85 pts), and commodity coffees with wsPFBc showed a different profile. The pulped (83 pts) and natural (82 and 88 pts) control coffees were the most preferred. These coffees were characterized by the flavor of almonds and nuts, milk chocolate, and brown sugar (FIG. 6).

The invention claimed is:

1. A method for enhancing flavour profile of beverages comprising:
   (A) increasing perceptibility of sweetness, increasing acidity, and decreasing astringent taste in beverages, and
   (B) increasing perceptibility of floral and spice notes
   wherein the method steps comprises: adding an effective flavour enhancing amount of water-soluble Palm Fruit Bioactive complex/Oil Palm Phenolics (wfPFBc/OPP) or their extracts into a beverage; and wherein the effective flavour enhancing amount is 1 to 5% of the beverage and wherein the effective flavour enhancing has polyphenol in a concentration of 20-80 mg per gram of wsPFBc/OPP or their extracts.

2. The method of claim 1, wherein said beverage includes coffee.

3. The method of claim 2, wherein said coffee is commodity coffee.

4. The method of claim 3, wherein said effective flavour enhancing has polyphenol at a concentration of 30 mg per gram of wsPFBc/OPP or their extracts.

5. The method of claim 4, wherein said effective flavour enhancing amount is added in an amount of 3% of the commodity coffee.

6. The method of claim 2, wherein said coffee is specialty coffee.

7. The method of claim 6 wherein said effective flavour enhancing has polyphenol at the concentration 40 mg per gram of wsPFBc/OPP or their extracts.

8. The method of claim 7, wherein said effective flavour enhancing amount is added in an amount of 3% of the specialty coffee.

9. The method of claim 1, wherein said effective flavour enhancing has polyphenol in a concentration of 30-40 mg per gram of wsPFBc/OPP or their extracts.

10. A method for enhancing flavour profile of coffee comprising:
    roasting coffee beans to produce roasted coffee beans;
    grinding said roasted coffee beans;
    preparing a coffee beverage composition using the roasted coffee beans;
    increasing perceptibility of sweetness, increasing acidity, and decreasing astringent taste in said coffee beverage composition, and increasing perceptibility of floral and spice notes by adding an effective flavour enhancing amount of water-soluble Palm Fruit Bioactive complex/Oil Palm phenolics (wsPFBc/OPP) or their extracts into said coffee beverage composition, ground coffee beans, or roasted coffee beans wherein the effective flavour enhancing amount is 1 to 5% of the whole wsPFBc and coffee beverage composition and the effective flavour enhancing has polyphenol in a concentration of 20-80 mg per gram of wsPFBc/OPP or their extracts.

11. The method of claim 10, wherein the coffee beverage is prepared from ground coffee, a granule mix, a powder mix, powder concentrates, a liquid mix, and liquid concentrates.

12. The method of claim 10, wherein the coffee beverage composition is selected from
    an instant coffee mix, an instant coffee beverage, brewed coffee, espresso, espresso-based coffee beverages, and cold brew.

13. The method of claim 12, wherein the coffee beverage composition is selected from:
    ground coffee, a granule mix, a powder mix, powder concentrates, a liquid mix, and liquid concentrates.

* * * * *